(12) United States Patent
Altshuler et al.

(10) Patent No.: US 10,130,450 B2
(45) Date of Patent: Nov. 20, 2018

(54) METHOD AND APPARATUS FOR LASER INDUCED THERMO-ACOUSTICAL STREAMING OF LIQUID

(71) Applicant: Laser Abrasive Technologies, LLC, Walpole, MA (US)

(72) Inventors: Gregory B. Altshuler, Lincoln, MA (US); Andrei V. Belikov, St. Petersburg (RU); Alexei V. Skrypnik, St. Petersburg (RU)

(73) Assignee: IPG Photonics Corporation, Oxford, MA (US)

( * ) Notice: Subject to any disclaimer, the term of this patent is extended or adjusted under 35 U.S.C. 154(b) by 1091 days.

(21) Appl. No.: 14/120,355

(22) Filed: May 14, 2014

(65) Prior Publication Data
US 2014/0342303 A1 Nov. 20, 2014

Related U.S. Application Data

(60) Provisional application No. 61/823,069, filed on May 14, 2013.

(51) Int. Cl.
*A61C 17/02* (2006.01)
*A61C 5/50* (2017.01)
*A61C 1/00* (2006.01)

(52) U.S. Cl.
CPC ........ *A61C 17/0202* (2013.01); *A61C 1/0046* (2013.01); *A61C 5/50* (2017.02); *A61C 17/02* (2013.01); *A61C 1/0069* (2013.01)

(58) Field of Classification Search
CPC ... A61B 18/26; A61B 18/28; A61B 2018/263; A61B 2018/266
USPC ........ 606/2.5, 3, 13–17; 433/29–31; 216/58, 216/71
See application file for complete search history.

(56) References Cited

U.S. PATENT DOCUMENTS

| | | | | |
|---|---|---|---|---|
| 6,709,269 B1* | 3/2004 | Altshuler | ............. | A61C 1/0046 433/215 |
| 8,956,343 B2* | 2/2015 | Belikov | ............... | A61B 18/201 606/2 |
| 2008/0054176 A1* | 3/2008 | Hiraoka | ................ | H01J 49/164 250/288 |
| 2008/0154157 A1* | 6/2008 | Altshuler | ............... | A61B 18/26 601/2 |
| 2010/0160838 A1* | 6/2010 | Krespi | ................... | A61B 18/26 601/15 |

(Continued)

*Primary Examiner* — Ahmed Farah
(74) *Attorney, Agent, or Firm* — Patentbar International, P.C.

(57) ABSTRACT

A laser induced thermo-acoustical system has a waveguide for propagating laser radiation to an absorbing layer of a tip. The tip has an absorbing layer serving to absorb the laser radiation propagating through the waveguide. The absorbing layer has such an absorption coefficient that upon absorbing the laser radiation the absorbing layer heats up to boil a quantity of a liquid when the tip is surrounded by the liquid. A laser induced thermo-acoustical method calls for providing a waveguide for propagating laser radiation to the absorbing layer of the tip to be at least partially absorbed by the absorbing layer and to boil a quantity of the liquid surrounding the tip and generating the stream of liquid. The laser induced thermo-acoustical streaming of the liquid is used, in particular, for the treatment of a root canal and periodontal pockets.

10 Claims, 7 Drawing Sheets

(56) References Cited

U.S. PATENT DOCUMENTS

| | | | |
|---|---|---|---|
| 2012/0301842 A1* | 11/2012 | Altshuler | A61C 1/0046 |
| | | | 433/29 |
| 2013/0066263 A1* | 3/2013 | Yoh | A61M 5/30 |
| | | | 604/70 |
| 2017/0074760 A1* | 3/2017 | Iida | C12M 35/02 |

* cited by examiner

METHOD AND APPARATUS FOR LASER INDUCED THERMO-ACOUSTICAL STREAMING OF LIQUID

RELATED APPLICATIONS

This application claims priority to Provisional Patent Application U.S. 61/823,069, filed May 14, 2013, which is incorporated herein by reference in its entirety.

BACKGROUND OF THE INVENTION

Lasers are widely use in various fields, including medical applications for soft and hard tissue treatment. Some laser applications often call for transformation of laser energy into acoustical energy. For example, such applications as laser thrombolysis, laser lithotripsy, laser root canal treatment and periodontal pocket debridement utilize laser induced bubble formation, shockwave generation and cavitation. Those applications call for a pulse laser with a selective wavelength which is highly absorbed by chromophores in the tissues, like water or blood. For example, Ho or I'm lasers have a wavelength at which those lasers are highly absorbed by water, so they are widely used for laser lithotripsy to remove impacted stones from the urinary tract by creating bubble and shockwaves that causes fragmentation of the stone (VersaPulse PowerSuite, Lumenis Ltd., Yokneam, Israel).

The Er laser with a wavelength at which that laser is extremely highly absorbed by water is used for treating root canals, root debridement of periodontal pockets, caries removal and other dental applications. For example, Er laser can induce bubbles formed in the water contained in the pulp chamber and root canal (WaterLase, BioLase, Inc., Irvine, Calif., USA; LighWalker, Fotona d.d, Ljubljana, Slovenia, EU). The drawback of those lasers is their high cost that limits their application in various fields, especially in dentistry. The need, therefore, exists to develop a new laser acoustical converter that can be used in various fields at a significantly lower cost.

SUMMARY OF THE INVENTION

The present invention is directed to a laser-induced thermo-acoustical system comprising a laser source and a tip, the tip comprising a waveguide for propagating laser radiation to an absorbing layer of the tip, the absorbing layer serving to absorb the laser radiation propagating through the waveguide and having such an absorption coefficient that upon absorbing the laser radiation the tip boils a quantity of a liquid when the tip is surrounded by the liquid. It is contemplated that the tip is a thermo-optical tip, the laser radiation is generated by a diode laser.

The absorbing material is selected from the group consisting of a semiconductor, metal, metal oxide, carbon, and doped optical material. The absorption coefficient is selected from a range from about 0.5 to about 1.0. Preferably, the absorption coefficient is selected from a range from about 0.8 to about 1.0. The thickness of the absorbing layer is selected from a range from about 0.01 mm to about 0.5 mm. Preferably, the thickness of the absorbing layer is selected from a range from about 0.05 mm to about 0.2 mm. The absorbing layer is disposed on a distal end of the tip, or on a side of the tip.

The absorption layer has a shape influencing diversion of streaming of the liquid.

The wavelength of the laser radiation is selected from a range corresponding to a lower absorption coefficient of a material of the waveguide and to the absorption coefficient of the absorbing material of the tip. The laser radiation has a pulse width selected from a range of 0.001 ms to 100 ms, a repetition rate selected from a range of 1 Hz and 10000 Hz, energy per pulse from a range of 5×S J/cm$^2$ to 500×S J/cm$^2$, wherein S is an area of a waveguide aperture, a laser power selected from a range of 20 W to 1000 W, and wherein incident fluence on the absorbing layer is from a range of 5 J/cm$^2$ to 500 J/cm$^2$.

Preferably, the laser radiation has a pulse width selected from a range of 0.05 ms to 10 ms, a repetition rate selected from a range of 1 Hz and 100 Hz, energy per pulse from a range of 10×S J/cm$^2$ to 100×S J/cm$^2$, wherein S is an area of a waveguide aperture, a laser power selected from a range of 50 W to 250 W, and wherein incident fluence on the absorbing layer is from a range of 10 J/cm$^2$ to 100 J/cm$^2$.

The present invention is also directed to a laser induced thermo-acoustical apparatus comprising a source of laser radiation; a tip comprising a waveguide for propagating the laser radiation to the absorbing layer of the tip, the absorbing layer serving to absorb the laser radiation propagating through the waveguide and having such an absorption coefficient that upon absorbing the laser radiation the tip boils a quantity of a liquid when the tip is surrounded by the liquid; and a water pump for pumping the liquid to the tip through a water channel. The laser radiation is generated by a diode laser. Furthermore, the apparatus further comprises a hand piece, and wherein the source is housed in the hand piece.

The method of the present invention is directed to a laser radiation induced thermo-acoustical method of generating a stream of liquid. Specifically, the method comprises providing a laser source and a tip comprising a waveguide for propagating the laser radiation to the absorbing layer of the tip; propagating the laser radiation through the waveguide to be at least partially absorbed by the absorbing layer; and utilizing the tip to boil a quantity of the liquid surrounding the tip and generating the stream of liquid; wherein the absorbing layer of the tip has such an absorption coefficient that upon absorbing the laser radiation the tip boils a quantity of a liquid.

The referenced method utilizes laser radiation has a pulse width selected from a range of 0.001 ms to 100 ms, a repetition rate selected from a range of 1 Hz and 10000 Hz, energy per pulse from a range of 5×S J/cm$^2$ to 500×S J/cm$^2$, wherein S is an area of a waveguide aperture, a laser power selected from a range of 20 W to 1000 W, and wherein incident fluence on the absorbing layer is from a range of 5 J/cm$^2$ to 500 J/cm$^2$. Preferably, the laser radiation has a pulse width selected from a range of 0.05 ms to 10 ms, a repetition rate selected from a range of 1 Hz and 100 Hz, energy per pulse from a range of 10×S J/cm$^2$ to 100×S J/cm$^2$, wherein S is an area of a waveguide aperture, a laser power selected from a range of 50 W to 250 W, and wherein incident fluence on the absorbing layer is from a range of 10 J/cm$^2$ to 100 J/cm$^2$.

BRIEF DESCRIPTION OF THE DRAWINGS

The accompanying drawings incorporated in and forming a part of the specification, illustrate the present invention, and together with the description serve to explain the principles of the invention.

DETAILED DESCRIPTION OF THE PREFERRED EMBODIMENTS

The present invention uses a low-cost laser for thermo-acoustical streaming of liquid and for dental applications, including, but not limited to, cleaning and disinfecting tissues, including root surfaces in periodontal pockets and root canals with accessory canals. The laser-induced thermo-acoustical streaming of liquid can be used for hard and soft tissue cutting in medical and veterinary applications.

Figure 1:
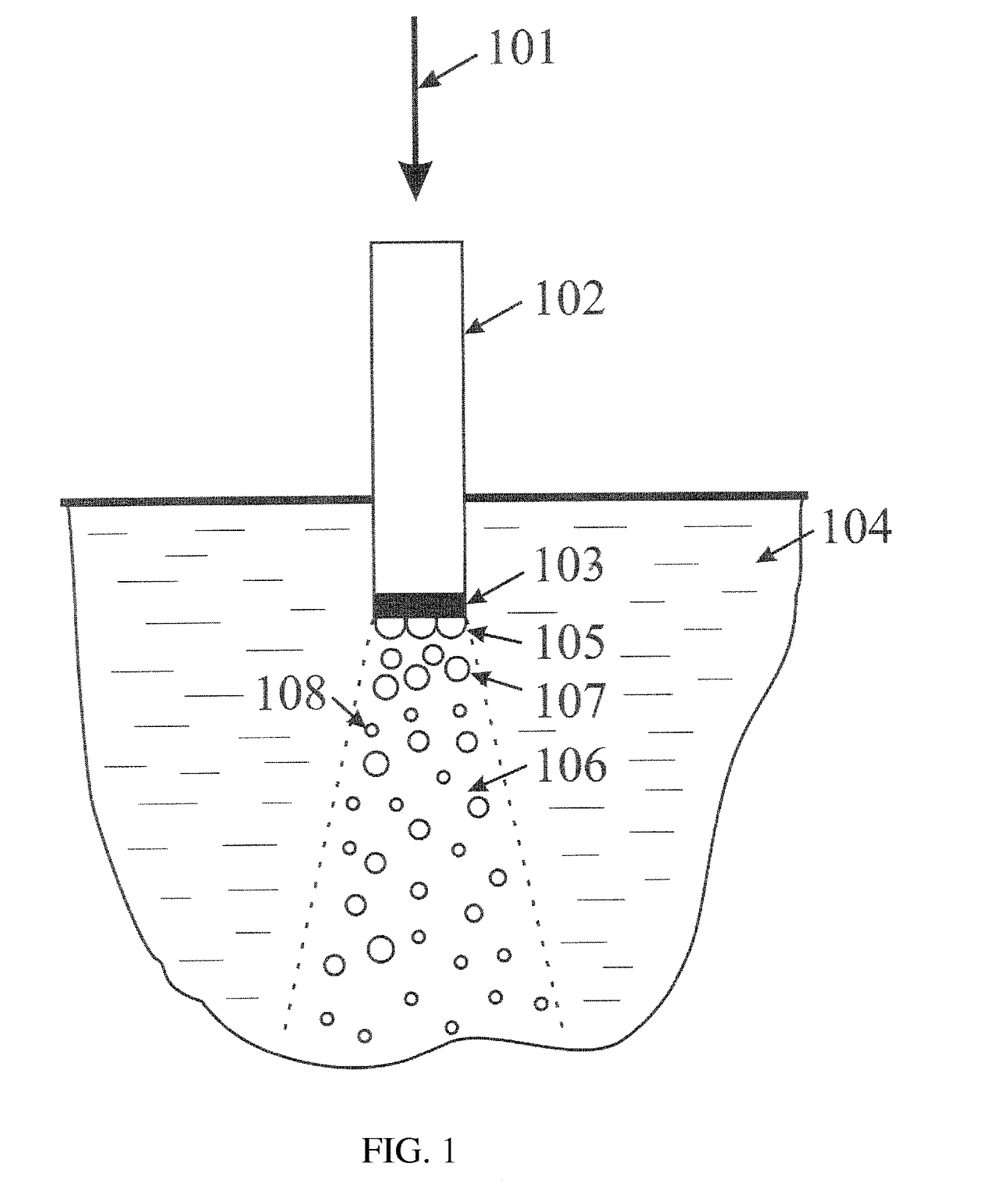
FIG. 1 shows a thermo-optical tip and laser thermo-acoustical streaming in liquid.

Laser-induced thermo-acoustical streaming of liquid is formation of directional high-pressure high-speed flow of liquid induced by rapid water vaporization and formation of bubbles in the liquid. FIG. 1 shows the mechanics of laser-induced thermo-acoustical streaming of liquid. Laser radiation 101 coupled in a waveguide 102 propagates to its distal end having a thin layer 103 of material highly absorbent for the laser radiation. The laser radiation heats up the layer 103 and, due to thermal conduction and thermal radiation, raises the temperature of the surrounding liquid 104 to the vaporization temperature. A bubble or bubbles 105 of vapor of the liquid grow on the surface of the absorptive layer 103. The bubbles expand rapidly creating a high positive acoustical pressure and rapid displacement of the liquid at high temperature and high speed. This results in a high-speed liquid flow or stream 106 with a high temperature near the vaporization temperature of the liquid. After the bubbles 105 begin to form, the heat conduction from the layer 103 decreases, this limits the size of the bubbles. The bubbles 105 may split up into smaller bubbles 107 or collapse. The negative pressure due to the bubbles 103 collapsing may cause cavitation and formation of cavitation bubbles 108. The stream of liquid 106 with high temperature, pressure, and speed of displacement consists of micro-bubbles 107 and 108. This laser-induced thermo-acoustical stream of liquid has a variety of strong mechanical and biological effects: tissue cells activation, damage, and/or destruction; bacteria deactivation, damage, and or destruction; decontamination of hard tissue surfaces; and cutting soft and hard tissue.

Figure 2A:
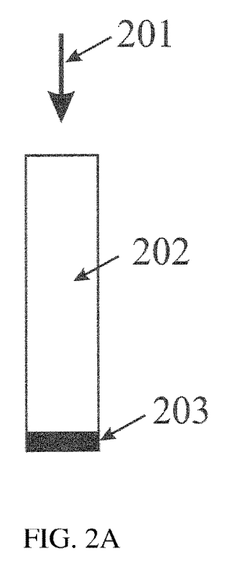
FIGS. 2a, 2b and 2c show configurations of thermo-optical tips with different directions of laser-induced thermo-acoustical streaming.
Figure 2B:
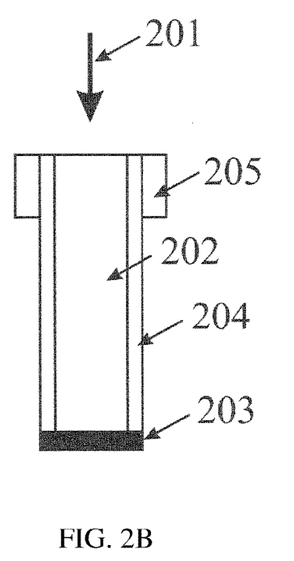
Figure 2C:
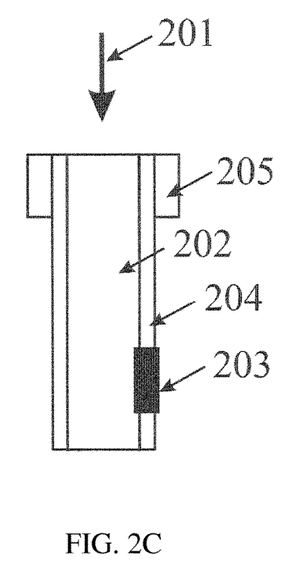

FIG. 2 shows example configurations of the waveguide 102 with the absorbing layer 103. The main function of this element is a fast and effective transfer and transformation of laser radiation into thermal energy within the liquid in contact with it. This thermo-laser (optically) powered element is called a thermal optical tip. FIG. 2 shows schematically several thermal optical tips. The optical waveguide 202 may be made of fused silica (quartz), glass, or crystal, such as sapphire, ceramic, composite material, or another optical material. This material has a low coefficient of absorption of laser radiation ($<0.05$ cm$^{-1}$, preferably $<0.005$ cm$^{-1}$). The waveguide may be, for example, a round cylinder or a prism. The waveguide may be, for example, an optical fiber with a core 202, cladding 204 and a buffer 205. A layer of absorbing material 203 may be located on the distal end (FIGS. 2a and 2b) for the stream parallel to the waveguide's axis or on a lateral surface (FIG. 2c) of the waveguide for the stream perpendicular to the waveguide's axis (a lateral thermo-optical tip). The absorbing layer 203 may be a highly absorbing structure, such as a semiconductor, metal, metal oxide, carbon, or doped optical material reliably attached to the waveguide 202 by sintering, infusion, ion diffusion, bonding, or another strong attachment method. The absorbing layer 203 may be formed in the core material, for example, by heating, vacuum, or chemical deposition or by ion diffusion. For example, it may be a layer of Si, or of SiC nanocrystals in fused silica, or a waveguide made of a transparent glass or crystal doped with ions absorbing optical radiation. A variety of metal ions, such as Ti, Cu, Nd, Ho, Tm, Cr, Fe, Yt, Er, Au, Ni, and others, may be used to form the absorptive layer. In other embodiments, the optical waveguide 202 may be a hollow glass or a metal waveguide with the absorbing element 203 being a metal cup. The tip may be designed so that the laser radiation passes partially through the absorbing layer. The absorption coefficient of the absorbing layer for laser wavelengths may be from 0.5 to about 1 and, preferably, from 0.8 to about 1. The diameter of the waveguide may be from 0.05 to 2 mm with preferable range from 0.2 to 0.4 mm. The thickness of absorptive layer may be from 0.01 to 0.5 mm, preferably, from 0.05 to 0.2 mm. The length of the tip may be from 1 to 40 mm. In some embodiments, the tip may be a distal part of the fiber cable for delivery of laser radiation from the laser to the distal end with an absorptive layer.

For some embodiments, the thermal optical tip manufacturing comprises three stages. During the first stage the absorptive centers on the distal surface of the waveguide 202 are created and embedded into the waveguide. At this stage, the distal edge of the waveguide is a piece of silica core/silica clad/gold coated fiber (such as from Fiberguide Industries, Inc., NJ, USA) in contact (under some pressure) with an absorptive medium comprising absorptive centers. Laser radiation heats up the medium to the temperature of softening or melting of the glass or quartz within the thermal optical tip or close to the temperature of melting of quartz. The absorptive centers may be powders or pressed carbon particles including nanoparticles, organic compounds, metals, metal oxides, and others. The heated absorptive centers stick to the surface of the softened tip material, creating bonding between the absorbing centers in the working edge of the tip at the end of the absorptive medium. The depth of immersion of the absorptive centers defines the thickness of tip region having the increased absorption (absorptive layer). The temperature and temperature application time are very important parameters because they should be high enough for the tip material softening, but not enough for its melting or evaporation. During this stage, the temperature of the distal end can be controlled by an infrared sensor or other method. For example, for quartz, the temperature should be held in the range of 1000-1700° C., preferably 1200-1600° C. The temperature control may be achieved by close-loop control which decreases laser power when the thermal radiation's intensity exceeds a target level and increases the laser power when the thermal radiation is below the target. The duration of the first stage of the thermo optical tip manufacturing may be between 0.1 and 10 sec.

The second stage of the thermo optical tip manufacturing involves cleaning. The purpose of the second stage is to remove insufficiently integrated absorptive centers from the tip. The cleaning is performed mechanically or chemically not involving laser radiation, but rather using a tissue or brush, possibly with a cleaning compound, for example, alcohol or an acid. The cleaning can be performed with a high pressure gas or liquid. The second stage can be eliminated by precise control of initial thickness of absorbing material during the first stage, if no excessive material is accumulated on the tip. The second stage can be eliminated, for example, by precise control of the amount of absorbing centers attached to the tip.

The third stage of the thermo optical tip manufacturing involves annealing of absorptive centers. The purpose of the third stage is homogenization of the dimensions of absorptive centers. Another goal of the third stage may be an improvement of adhesion between the absorber and the material of the thermal optical tip, thermal inducement of diffusion of absorber, sintering between the absorber and the material of the thermal optical tip, and relaxation of mechanical stress within the thermal optical tip. One mechanism of homogenization involves burning out the absorptive centers having maximum limit of size because large absorptive centers have high absorption cross-section and, therefore, absorb more laser energy than small ones. Thus, the laser power should be high enough for burning out (i.e. evaporating) the large centers and not enough for burning out of small ones. During this stage, laser radiation can be applied to the tip exposed in the air.

It is also helpful to use an optical feedback mechanism during the first and third stages of the tip manufacturing to maintain the tip temperature at an optimal level. The optimal level of the temperature is different for the burn-in stage and for the annealing stage. For example, the optimum temperature at the third stage can be in the range of 600-1000° C. This process takes place under the tip temperature control. The level of thermal radiation critical for annealing is lower than the level of thermal radiation critical for "blackening". While the number of large centers decreases, it is necessary to apply more laser power to maintain the level of thermal radiation critical for annealing. If the tip is made of quartz fiber with a diameter of 400 the duration of the third stage may be about 0.1-10 s and the third stage consists of up to 50 cycles with the cycle length of about 0.05-100 ms.

The shape of the waveguide 202 where it is covered by the absorptive layer 203 may be designed to control the divergence of laser thermo-acoustical streaming. It can have a positive curvature or a conical shape to increase the divergence of liquid streaming and to decrease the pressure and speed of water displacement in the steaming direction and to obtain a more uniform distribution of acoustical power. A negative curvature or conical shape can be used to decrease the divergence of liquid streaming and to increase the pressure and speed of water displacement in the direction of steaming.

A variety of lasers or of non-laser light sources can be used for heating the absorptive layer. The wavelength of the laser should be within the range overlapping the high absorption of absorptive centers in 203 and the low absorption of the waveguide material 202. For example, for the carbon particles and the silica material of the waveguide this range is from 300 to 2700 nm. The laser-induced thermo-acoustical streaming of liquid involves a combination of several physical mechanisms, such as non-stationary laser heating of the absorptive layer with a non-regular surface, heating of liquid through heat conduction and heat radiation, vaporization and bubble formation, the dynamics of the growth, collapse, or oscillation of individual bubbles in an otherwise quiescent liquid, positive and negative pressure dynamics in the liquid, possible shock wave formation, steaming of the liquid, motion of bubbles in the liquid, homogeneous bubbly flows with cloud cavitation, and other phenomena. A theoretical prediction of parameters of such a complex phenomenon is very difficult. For the present invention, these parameters had been determined by experimental discovery and phenomenological theoretical modeling.

Laser-induced thermo-acoustical streaming experiments were performed in water with a thermo-optical tip, such as a quartz fiber with core diameters of 0.2, 0.3, 0.4, and 0.6 mm with carbon nanoparticles sintered into the distal end of the fiber as described hereinabove. The absorption coefficient of the absorptive layer was from 0.8 to 0.96. A diode laser with a wavelength of 980 nm, power of up to 500 W, pulse width from 0.005 to 100 ms, repetition rate from 1 to 1000 Hz was used in the continuous wave mode. The threshold energy density for inducing laser-induced thermo-acoustical streaming in water was about 4 $J/cm^2$ when the pulse width is shorter than 0.1 ms. The threshold cumulative energy for laser-induced thermo-acoustical streaming in water depends on the tip diameter and is from 5 mJ to about 50 mJ for the tips used in the experiments.

Figure 3:
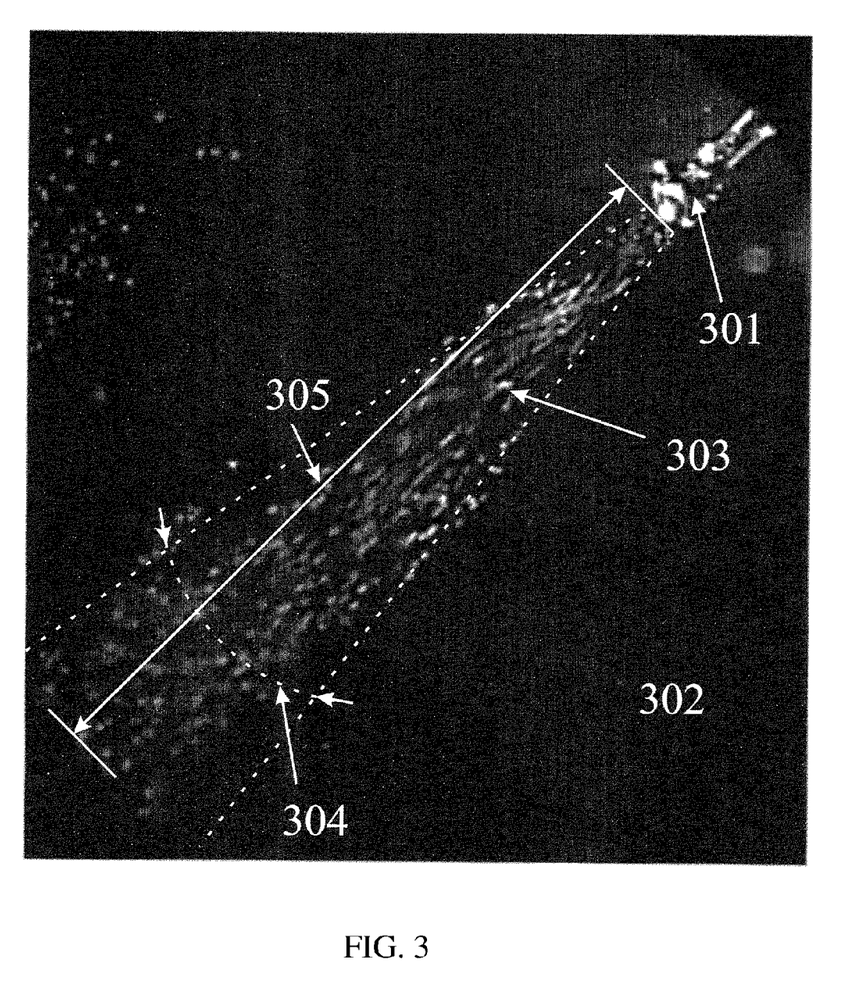
FIG. 3 shows laser-induced thermo-acoustical streaming of water.

A typical picture of laser-induced thermo-acoustical streaming in water taken with a high-speed camera with a side-flash pulse illumination is shown on FIG. 3. The thermo-optical tip 301 with a core diameter of 0.3 mm was pumped by a laser pulse with a 25 W peak power and 1 ms pulse width. The laser-induced thermo-acoustical streaming in water 302 consisted of a cloud of micro-bubbles 303. The laser-induced thermo-acoustical streaming can be described by a divergence angle 304 and length of propagation 305 defined as a distance between the distal end of the thereto optical tip and a point where the speed of water displacement is close to zero. The length of propagation, the pressure in the stream, and the speed of water displacement increases with the energy of laser pulse. The maximal values observed in this experiment is the length of steam propagation of up to 25 mm, the speed of displacement of up to 1 m/s, and the water pressure measured near the thermo-optical tip of up to 5 kbar. The divergence of streaming was 10° to 20°.

Figure 4:
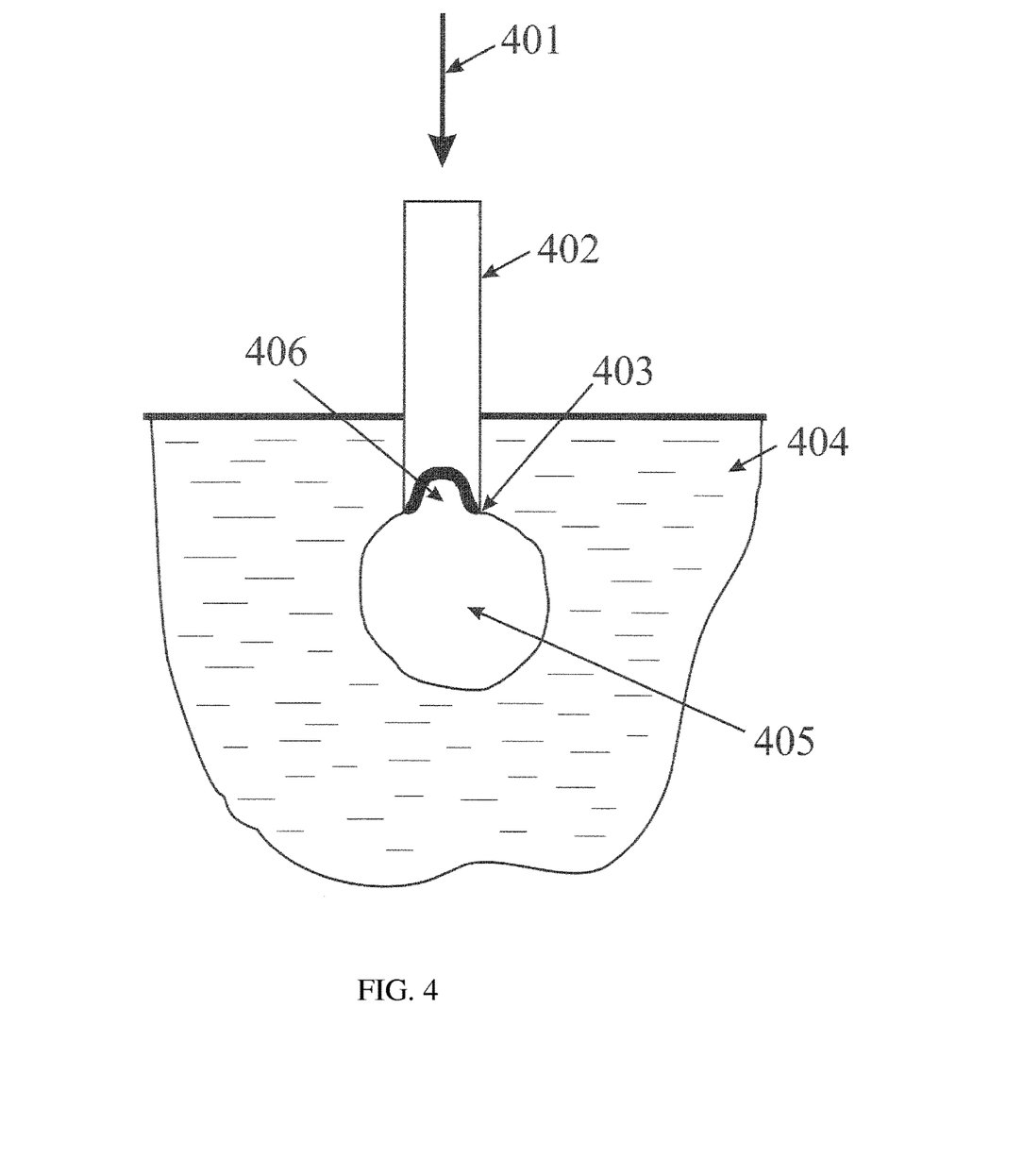
FIG. 4 shows a thermo-optical tip with a micro-chamber for large bubble and high-pressure generation.

The dynamics and the distribution of the laser-induced thermo-acoustical streaming depend on the shape of the distal end of the thermal optical tip. FIG. 4 shows one embodiment of the present invention for laser-induced thermo-acoustical bubble generation with a thermo optical tip. In this embodiment, the laser radiation 401 is coupled into the thermo optical tip consisting of the waveguide 402 with an absorptive layer 406 on the distal end of the waveguide. This tip has a semi-open cavity 406. This thermal optical tip was made out of a 0.32 mm silica core/polyamide clad fiber (Fiberguide Industries, Inc., NJ, USA) using the method described above to infuse pressed $TiO_2$ particles with the average size of about 5 μm, the temperature at the first stage being about 1600° C. and on the third stage being about 700° C. The cavity 406 ended up coated with an absorbed layer with Si and Ti ions. The cavity 406 localizes the heating of the liquid 404 in the semi-enclosed space for rapid vaporization of liquid in response to heating of the absorptive layer 403 by the laser radiation 401 and for formation of a mono-bubble 405 which can extend outside cavity 406. For experimenting with this tip a laser with the wavelength of 975 nm, the peak power of 25 W, and the pulse width from 0.005 to 100 ms. It was found that the threshold pulse width for bubble formation under these conditions is about 0.5 ms. When the pulse width is increasing to 1.5 ms, the bubble is growing outside the cavity 406 and continues to grow up to the maximal size of about 0.7 mm within 3 ms and collapses rapidly at 3.5 ms. After 3.5 ms, this process of bubble growing and collapsing is repeated again periodically. The periodical formation and collapse of the mono-bubble 405 leads to pressure oscillation within liquid from a high positive pressure to a low negative pressure in the surrounding liquid 405, as well as the streaming oscillations caused by the laser pulsing. The frequency of this oscillation was about 285 Hz. The frequency of the oscillation of pressure and of steaming in liquid can be increased by increasing the laser power and increasing the size of the tip. The maximal frequency of osculation is about 10000 Hz.

Such rapid large bubble formation can be achieved with direct heating of liquid with laser which has a wavelength that is highly absorbent for the liquid. For example, a Ho or Tm laser has a wavelength highly absorbent by water (about 200 cm$^{-1}$) and is widely used for the laser lithotripsy to remove impacted stones from the urinary tract by creating a bubble and shockwave causing fragmentation of the stone. The Er laser with a wavelength of higher water absorption (about 12000 cm$^{-1}$) used for root canal treatment using laser-induced bubble formation in water present in the pulp chamber and the root canal (WaterLase, BioLase, Inc., Irvine, Calif., USA; LighWalker, Fotona d.d, Ljubljana, Slovenia, Europe). The present invention can produce the same bubble formation using significantly less costly mechanisms because it does not require using Ho, Tm, or Er lasers with unique lasers wavelengths, but rather allows using low cost diode lasers.

The optimal regime for laser heating of the absorptive layer for the laser-induced thermo acoustical streaming is when the laser pulse is shorter than the approximate length of thermal relaxation within the absorptive layer. The thermal relaxation time (TRT) of an absorptive layer with a thickness of z mm positioned on a fused silica waveguide can be calculated by the formula: TRT=0.25·z$^2$. For a layer with the thickness of 0.01 mm, the TRT is 0.025 ms; and for a layer with the thickness of 0.2 mm, the TRT is 10 ms.

The parameters of laser radiation for the laser-induced thermo-acoustical streaming of liquid can be summarized as follows:

Laser wavelengths in the range overlapping the regions of high absorption by the absorptive center and low absorption by the waveguide material. The laser wavelength can be in from 300 nm to 2700 nm for the waveguide made of silica, and 300 nm to 11000 nm for a hollow waveguide.

The laser pulse width in the range from 0.001 ms to 100 ms. The preferable range is from 0.05 ms to 10 ms.

The repetition rate can be from 1 Hz to 10000 Hz. The preferable range is from 1 Hz to 100 Hz.

The energy fluence at the absorptive layer is from 5 J/cm$^2$ to 500 J/cm$^2$, preferably from 10 J/cm$^2$ to 100 J/cm$^2$.

The energy per pulse can be in the range from 5·S [J] to 500·S [J], preferably in the from 10·S [J] to 100·S [J], where S is the area of waveguide aperture in cm$^2$.

The power of the laser can be from 20 W to 1000 W, preferably from 50 W to 250 W.

Figure 5:
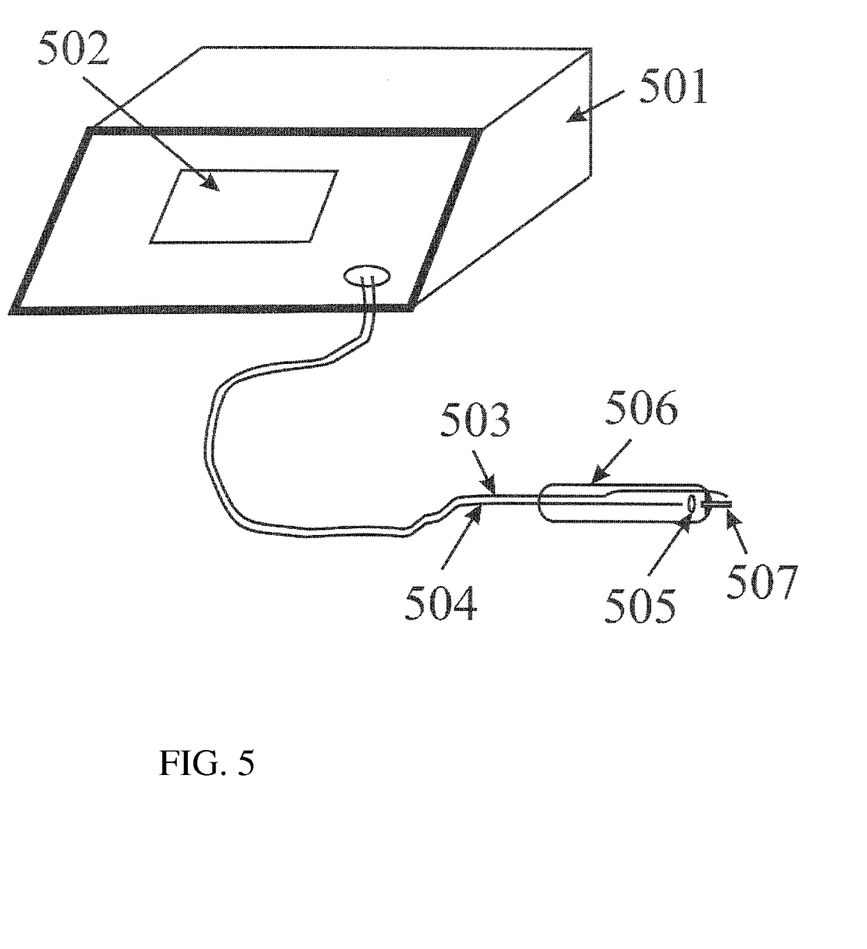
FIG. 5 shows an embodiment of an apparatus for laser-induced thermo-acoustical streaming in liquid.

One embodiment of the present invention, an apparatus for laser-induced thermo-acoustical streaming of liquid is shown in FIG. 5. The apparatus comprises of a main unit 501 with a power supply, a microcomputer, a water pump and a laser, a housing, and a display 502 (for example, Alta Modular Laser System, Dental Photonics, Inc., Walpole, Mass., USA), an umbilical with a water line and an optical fiber 504, a handpiece handle 506, a lens 505, and a thermal optical tip 507. The laser for the laser-induced thermo-acoustical streaming of liquid has the parameters as described hereinabove. The laser can be a diode laser, a fiber laser, a solid-state laser, or a gas laser. One preferable embodiment uses a GaAsAl semiconductor (diode) laser with a wavelength from 790 nm to 1100 nm with a fiber coupling. The preferable wavelength range is from 915 nm to 980 nm. A laser of this type has the lowest cost per watt of output power. Examples of lasers suitable for this embodiment include PLD-33, PLD-60, and PLD-100 from IPG Photonics, Inc., Oxford, Mass., USA. The cost per watt of such lasers is one or more orders of magnitude lower than the cost of lasers used for direct laser induced bubble formation in thrombolysis, lithotripsy (for example, Nd, Ho, or Tm lasers), or the cost of Nd or Er lasers used for root canal treatment. The liquid water line in some embodiment can be eliminated if the apparatus is used with other sources of water or if water is present in the treatment zone. In another embodiment, the laser can be mounted into a handpiece handle 506 with direct coupling of laser radiation into thermo optical tip.

Laser-induced thermo-acoustical streaming of liquid has a unique combination of properties including a high positive pressure (up to 10 kBar), a high speed of water motion (up several m/s), a cloud of microbubbles, a long distance of propagation (several centimeters in free liquid), a controllable divergence which can be very low (up to 10 degree), and a high temperature, which can be close to the boiling point (100° C. for water) on the entire propagation path. At the same time, the laser-induced thermo-acoustical streaming of liquid has very high precision due to the very small size of the thermo-optical tip and low divergence of the stream. Another important advantage of the laser-induced thermo-acoustical streaming of liquid is its capability to deliver this energy source to the treatment zone through flexible optical fiber. It is important for biomedical applications.

The laser-induced thermo-acoustical streaming of liquid has a strong mechanical and biological effect on tissue cells activation, tissue cell damage, bacteria deactivation or damage, and decontamination of hard tissue surface and can be used for cutting of soft and hard tissue. The laser-induced thermo-acoustical streaming can be used for periodontal and endodontic treatments, orthopedic surgery, cartilage, bone, and other tissue regeneration, lithotripsy and other applications in medicine, dentistry, and veterinary fields.

Figure 6:
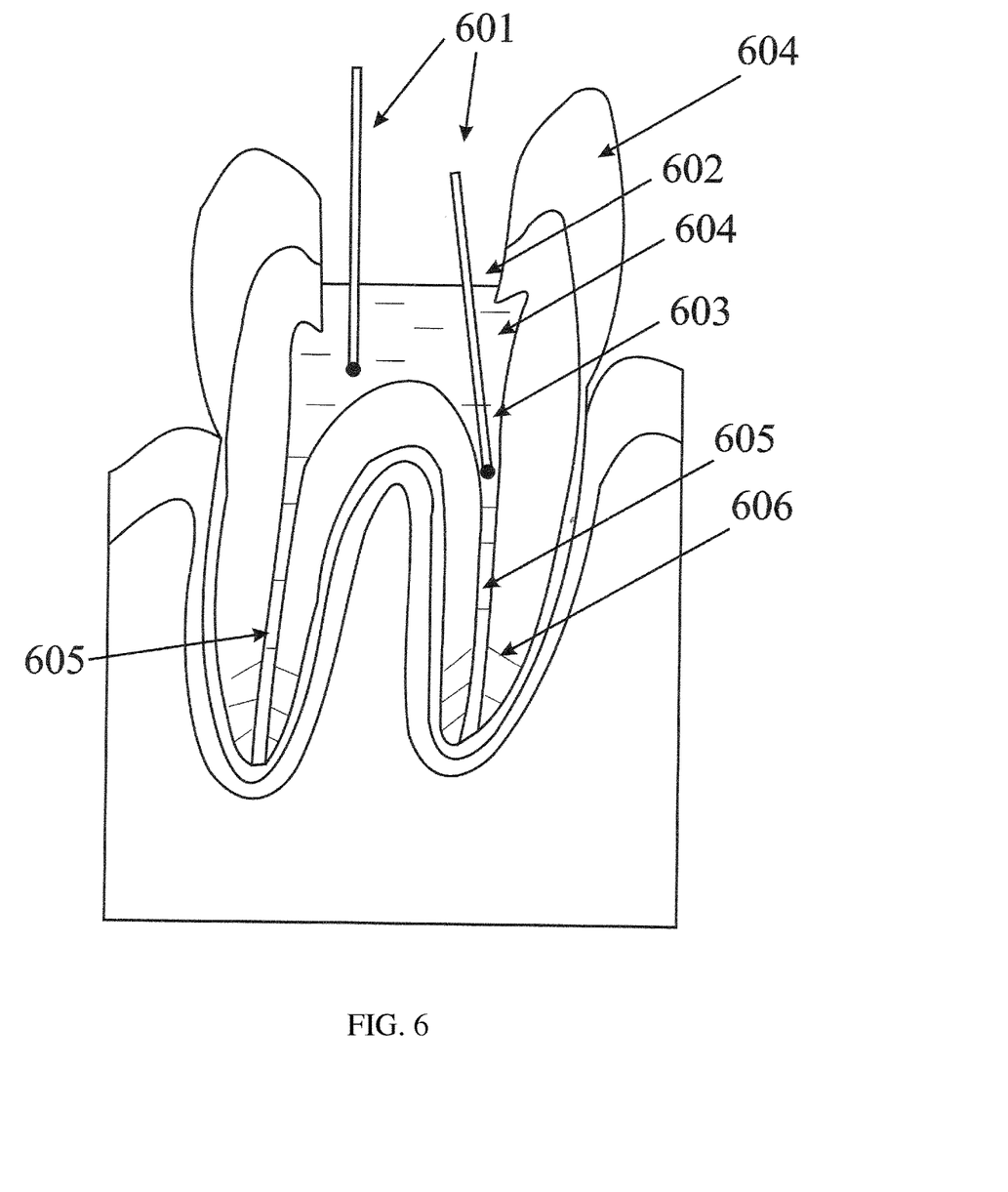
FIG. 6 shows application of laser thermo-acoustical streaming of liquid for root canal therapy.
Figure 7:
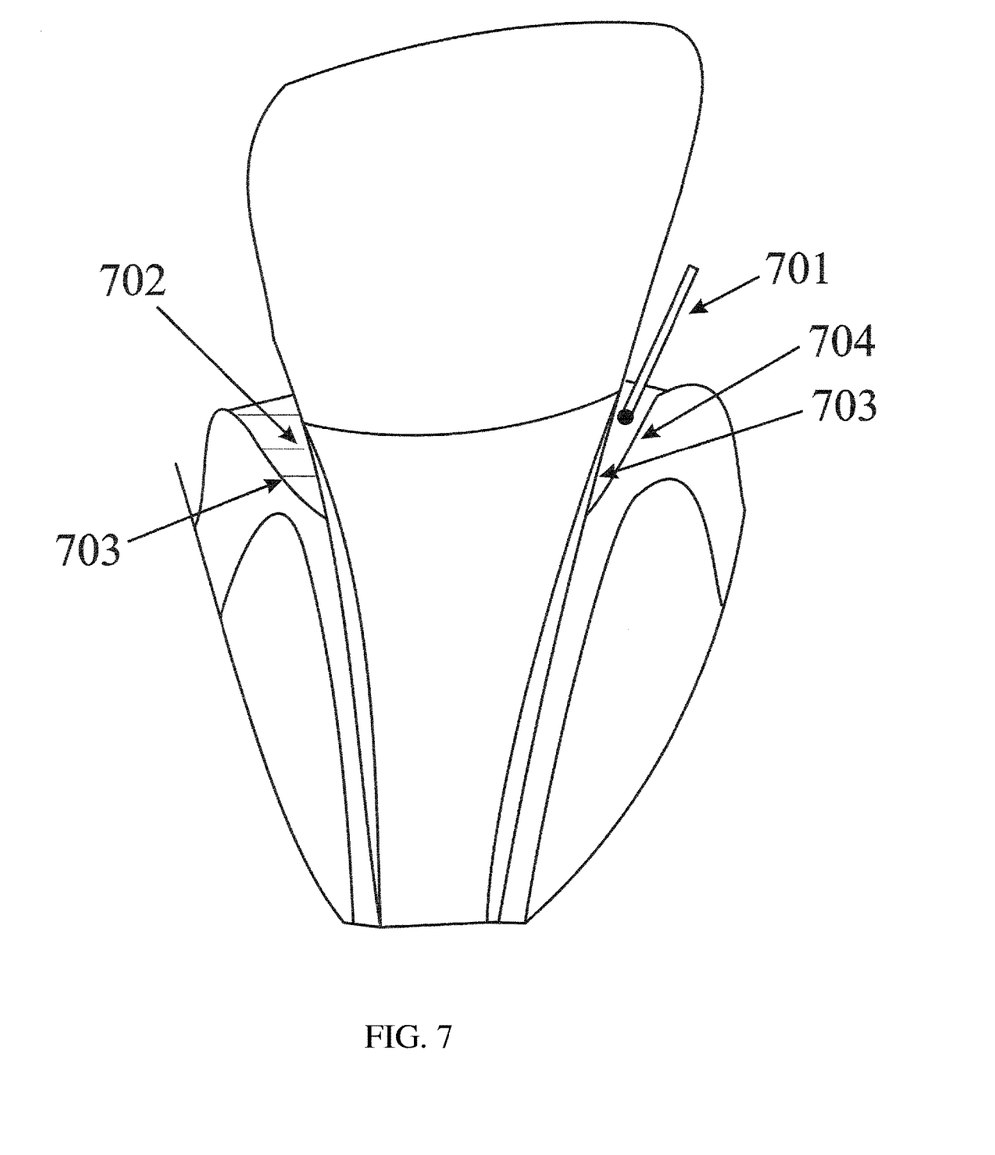
FIG. 7 shows application of laser thermo-acoustical streaming of liquid for periodontal therapy.

FIGS. 6 and 7 show schematic treatment of root canal and periodontal pocket. The root canal treatments require debriding or rendering harmless the tissue, bacteria, and viruses within a root canal and the surrounding dentin including accessory or lateral canals and dentine tubules. The current methods of root canal treatment have significant percentage of failures over time because of improper root canal cleaning and disinfection. The laser-induced thermo-acoustical steaming in the root canal therapy can be used for root canal cleaning and bacteria deactivation and destruction. The thermo-optical tip 601 is placed into the pulp chamber 602 or an upper put of root canal 603 of a tooth filled with water 604. The laser induced thermo acoustical streaming enters the root canal, cleans and removes the residual soft and hard tissues remaining from prior mechanical treatment and the smear layer produced by filing (if a file has been use before the laser treatment). The cleaning effect is due to the fast water motion within the canal 605, due to the high thermo-acoustical pressure and the oscillations. The local speed of water displacement in the laser-induced thermo-acoustical streaming can be up to 10 m/s, while the local flow within root canal is turbulent because the Reinhold criteria (Re>2300) is satisfied for the canal with a 1 mm diameter for water flow speeds of 2.3 m/s and for water flow speeds of 0.23 m/s for a canal with the diameter of 0.1 mm. An addition cleaning effect is provided by the oscillation of high pressure propagating into the lateral canals 606 and into the dentine tubules. The bacteria deactivation and destruction can occur simultaneously with the cleaning or continue afterwards. The thermo-optical tip 601 can be inserted into the root canal 603 filed with water or preferably with the sodium hypochlorite solution or with other medical liquid with a similar anti-bacterial effect 604. The mechanisms of bacteria deactivation and damaging are the thermal denaturation of bacteria proteins due to heating of high temperature water (70° C. to 100° C.), the effect of acoustical waves with negative amplitude pressure, the cavitation bubbles, the distraction of bacteria wall by acoustical wave and increasing penetration of the medicaments, enhancements of delivery of medicaments into lateral canals and dentinal tubules due to phonophoresis induced by thermal acoustical effect and increasing effect of medication on bacteria due high temperature. We have demonstrated in vitro and optimized laser parameters of cleaning of root canal of tooth. The parameters for root canal treatment with laser-induced thermo-acoustical streaming are: thermo optical tip diameter in the range from 0.05 to 0.3 mm, preferable range is 0.2 to 0.3 mm, peak laser power in the range from 25 to 500 W, pulse width in the range from 0.05 to 10 ms, average power in the range from 1 to 5 W, continues treatment time of one tooth in the range from 10 to 30 sec.

Treatment of periodontitis requires cleaning root surface in periodontal pocket by removing or eliminating dental plaque, its products, and calculus to establish a periodontium that is free of disease. This process provides with mechanical instrument as periodontal scalers and periodontal curettes and can be significantly improved by adding laser induced thermo acoustical streaming in periodontal pocket after mechanical cleaning. On FIG. 7 shown a diagram of treatment of periodontal pocket. Mechanism of cleaning effect is removing of residual plaque and calculus from root surface due turbulent water flow with cloud of micro bubbles and high pressure applied to these residuals. In additional laser induced thermo acoustical streaming provide effect of bacteria deactivation on root surface. Mechanisms of bacteria deactivation and damaging are thermal denaturation of bacteria proteins due heating by high temperature (70° C. to 100° C.) and effect of acoustical waves with negative amplitude pressure and cavitation bubble. Thermo optical tip 701 inserts in periodontal pocket and moved to cover uniformly root surface 702 with laser inducer thermo acoustical streaming in water 703. Simultaneously laser induced thermo acoustical streaming can provide removing of junctional and sulcular epitheliums 703 to grow new attachment of gingiva to the cementum of the root. The parameters of laser for periodontal therapy with laser induced thermo acoustical streaming are thermo optical tip diameter in the range from 0.2 to 0.6 mm, preferable range is 0.3 to 0.5 mm, peak laser power in the range from 25 to 500 W, pulse width in the range from 0.1 to 10 ms, average power in the range from 1 to 5 W, continues treatment time in the range from 10 to 60 sec.

What is claimed is:

1. A laser radiation induced thermo-acoustical method of generating a stream of a liquid, the method comprising:
    providing a laser source and a tip, the tip comprising a waveguide and an absorbing layer surrounded by a liquid;
    propagating laser radiation from the laser source through the waveguide to the absorbing layer;
    heating the absorbing layer in response to the absorbing layer absorbing a portion of the laser radiation; and
    boiling the liquid surrounding the absorbing layer, in response to heating the absorbing layer, to generate bubbles of vapor of the liquid and to generate acoustical pressure to generate the stream of the liquid,
    wherein the absorbing layer of the tip has an absorption coefficient that allows boiling of the liquid.

2. The method of claim 1, wherein the laser radiation has a pulse width selected from a range of 0.001 ms to 100 ms, a repetition rate selected from a range of 1 Hz and 10000 Hz, energy per pulse from a range of $5 \times S$ J/cm$^2$ to $500 \times S$ J/cm$^2$, wherein S is an area of an aperture of the waveguide, a laser power of the laser source is selected from a range of 20 W to 1000 W, and incident fluence on the absorbing layer is selected from a range of 5 J/cm$^2$ to 500 J/cm$^2$.

3. The method of claim 1, wherein the laser radiation has a pulse width selected from a range of 0.05 ms to 10 ms, a repetition rate selected from a range of 1 Hz and 100 Hz, energy per pulse from a range of $10 \times S$ J/cm$^2$ to $100 \times S$ J/cm$^2$, wherein S is an area of an aperture of the waveguide, a laser power of the laser source is selected from a range of 50 W to 250 W, and incident fluence on the absorbing layer is selected from a range of 10 J/cm$^2$ to 100 J/cm$^2$.

4. The method of claim 1, wherein the absorption coefficient ranges from 0.5 to 1.0.

5. The method of claim 1, wherein the absorption coefficient ranges from 0.8 to 1.0.

6. The method of claim 1, wherein a thickness of the absorbing layer ranges from 0.01 mm to 0.5 mm.

7. The method of claim 1, wherein a thickness of the absorbing layer ranges from 0.05 mm to 0.2 mm.

8. The method of claim 1, wherein the absorbing layer is disposed on a distal end of the tip.

9. The method of claim 1, wherein the absorbing layer is disposed on a side of the tip.

10. The method of claim 1, wherein the absorption layer has a shape influencing diversion of streaming of the liquid.

* * * * *